US00PP16158P2

(12) United States Plant Patent
Gossett

(10) Patent No.: US PP16,158 P2
(45) Date of Patent: Dec. 13, 2005

(54) ×*HEUCHERELLA* PLANT NAMED 'BIRTHDAY CAKE'

(50) Latin Name: ×*Heucherella* sp.
Varietal Denomination: Birthday Cake

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 127 days.

(21) Appl. No.: 10/871,737

(22) Filed: Jun. 18, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,159 P2 * 10/2001 Heims ..... Plt./263
PP13,701 P2 * 4/2003 Heims ..... Plt./263

OTHER PUBLICATIONS http://www.terranovanurseries.com/pages/plantsH6.html.*

* cited by examiner

*Primary Examiner*—Kent Bell
*Assistant Examiner*—W C Haas
(74) *Attorney, Agent, or Firm*—Klarquist Sparkman, LLP

(57) ABSTRACT

A new and distinct cultivar of ×*Heucherella* plant characterized by its mounding habit, chocolate colored, cut and ruffled leaves, and creamy flowers in candle-like spikes.

1 Drawing Sheet

Botanical designation: ×*Heucherella* sp.
Variety denomination: 'Birthday Cake'.

BACKGROUND OF THE INVENTION

The present invention relates to a new and distinct intergeneric hybrid between *Heuchera* and *Tiarella,* or ×*Heucherella,* and given the cultivar name 'Birthday Cake'. Both genera, *Heuchera* and *Tiarella,* are of the family Saxifragaceae.

This new cultivar originated as a single plant from crossing a group of selected *Heuchera* hybrids with massed pollen from a group of selected *Tiarella* hybrids. The specific parent plants are unknown.

SUMMARY OF THE INVENTION

This new ×*Heucherella* is characterized by:

1. Small, chocolate colored, ruffled and deeply cut leaves.
2. Creamy white flowers on brown peduncles, rising above the foliage like birthday candles.
3. Mounding habit.
4. Excellent vigor.

The new variety has been reproduced only by asexual propagation (division and tissue culture). Each of the progeny exhibits identical characteristics to the original plant. Asexual propagation by division and tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a two year old plant of the new variety growing in the trial field in Canby, Oreg.

DETAILED PLANT DESCRIPTION

The following is a detailed description of the new ×*Heucherella* hybrid based on observations of two-year-old specimens grown in the field in the ground in full sun under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical name: ×*Heucherella.*
Cultivar name: 'Birthday Cake'.
Plant:
- *Type.*—Herbaceous perennial.
- *Form.*—Basal rosette.
- *Hardiness.*—USDA Zone 5.
- *Size.*—17 cm tall from the ground to the top of the foliage and 40 cm wide.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Broadly ovate.
- *Lobing/division.*—3 to 5 lobed parted, with terminal cut almost to the petiole, with each lobe also lobed two to three times.
- *Venation.*—Palmate.
- *Margins.*—Deeply crenate and ruffled.
- *Apex.*—Acute.
- *Base.*—Cordate and sometimes overlapping.

*Blade size.*—Ranges from 6 cm to 7 cm long and 5.5 cm to 6 cm wide.

*Surface texture.*—Soft with glandular hairs.

*Petiole size.*—Ranges from 10 to 11 cm long and 2 mm wide.

*Petiole surface.*—Glandular hairs.

*Petiole color.*—Greyed Orange 176A.

*Leaf color.*—Topside: Brown, closest to Brown 200B and darkening at main veins to Brown 200A. Bottom side: Burgundy, closest to Greyed Purple 187A, but lighter.

Inflorescence:

*Type.*—Thyrse.

*Number of thyrse in first flush in spring.*—25 to 40.

*Number of flowers.*—Ranges from 50 to 70 per thyrse, on top 8 cm of peduncle.

*Peduncle.*—Unbranched with 1 to 2 small leaves. Height — 35 cm. Diameter — 0.25 cm. Color — Burgundy to brown, Greyed Purple 183B to Greyed Orange 165A. Surface texture — Glandular hairs.

*Pedicel.*—Length — up to 0.4 cm. Surface texture — Glandular hairs. Color — Greyed Purple 187B.

*Bloom period.*—May to June in Canby, Oreg.

Flower bud:

*Size.*—0.2 cm deep and 0.2 cm wide.

*Description.*—Oblong, downfacing, glandular pubescent.

*Color.*—Tan, Greyed Orange 165C.

Flower:

*Type.*—Complete, sepals petaloid.

*Shape.*—Rotate.

*Flower size.*—0.4 cm wide and 0.4 cm deep.

*Petals.*—5, inconspicuous, Yellow White 158A on inner and outer surfaces, spatulate in shape, size is 1.5 mm long and 0.7 mm wide, margins are entire, apex is acute.

*Calyx.*—Petaloid, rotate in shape, 4 mm wide and 2 mm deep divided ½ way to the base, with glandular hairs, sepal lobes are ovate with an acute apex, margins entire, cream-colored, Yellow White 158A on both surfaces, slightly duller on back surface.

*Stamen.*—5 in number, sterile, filaments of Yellow White 158A are 3 mm deep terminated with oval, flattened anthers, 0.1 mm wide and 0.15 mm deep, no pollen produced.

*Pistil.*—15 mm long and 2.5 mm wide, Yellow White 158A overall, ovoid and two-lobed, each lobe is 1 mm long terminated in a narrow stigma.

*Fragrance.*—None.

*Lastingness.*—A thyrse blooms for about 2 weeks on the plant.

Fruit and seed: None. The plant does not form fruit or seed.

*Fertility.*—Sterile.

Disease and pest tolerance: Excellent disease resistance to *Heuchera* rust and powdery mildew. ×*Heucherella* are susceptible to root weevils.

COMPARISONS TO SIMILAR ×*HEUCHERELLA*

Compared to *Heucherella* 'Burnished Bronze' (U.S. Plant Pat. No. 12,159), this new cultivar has smaller, lighter, more divided and ruffled leaves as well as cream rather than pink to white flowers.

Compared to ×*Heucherella* 'Chocolate Lace' (U.S. Plant Pat. No. 13,701), the new cultivar has more vigor, a rounder, more mounding habit, ruffled leaves instead of unruffled, and cream rather than white flowers.

I claim:

1. A new and distinct cultivar of ×*Heucherella* plant as herein illustrated and described.

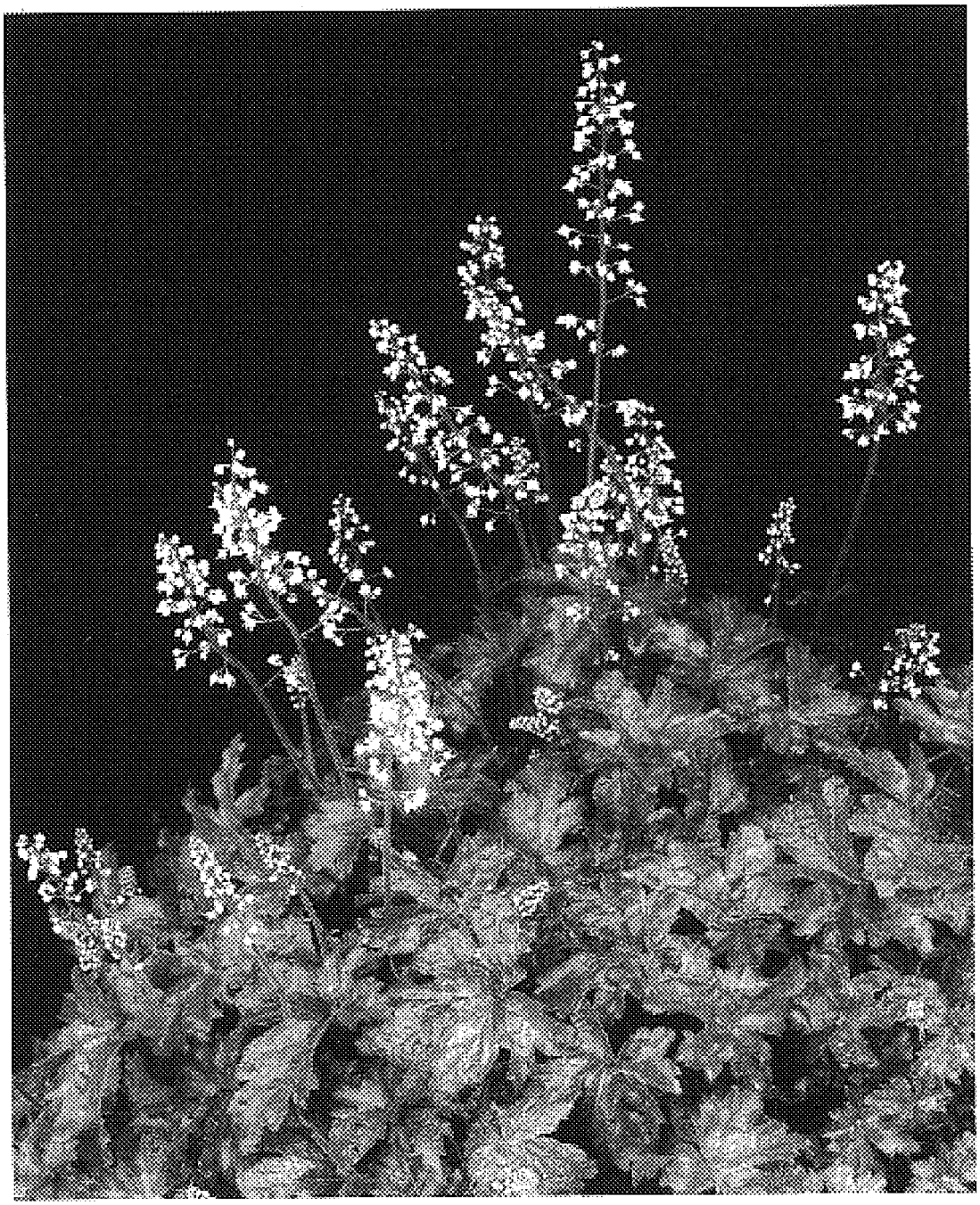

* * * * *